(12) United States Patent
Bani-Hashemi et al.

(10) Patent No.: US 8,280,002 B2
(45) Date of Patent: Oct. 2, 2012

(54) RADIATION TREATMENT OF MOVING TARGETS

(75) Inventors: Ali-Reza Bani-Hashemi, Walnut Creek, CA (US); Francisco Miguel Hernandez-Guerra, Concord, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 169 days.

(21) Appl. No.: 12/828,530

(22) Filed: Jul. 1, 2010

(65) Prior Publication Data

US 2012/0002786 A1    Jan. 5, 2012

(51) Int. Cl.
*A61N 5/10* (2006.01)
(52) U.S. Cl. ............................................. 378/65; 378/95
(58) Field of Classification Search .................... 378/62, 378/64, 65, 68, 69, 95
See application file for complete search history.

(56) References Cited

U.S. PATENT DOCUMENTS

| | | | |
|---|---|---|---|
| 5,818,902 A | 10/1998 | Yu | |
| 7,469,035 B2 | 12/2008 | Keall et al. | |
| 7,609,810 B2 | 10/2009 | Yi et al. | |
| 2005/0059887 A1 | 3/2005 | Mostafavi et al. | |
| 2007/0076846 A1 | 4/2007 | Ruchala et al. | |
| 2008/0226030 A1 | 9/2008 | Otto | |

FOREIGN PATENT DOCUMENTS

WO    WO 02/19908    3/2002

OTHER PUBLICATIONS

EP Search Report dated Oct. 18, 2011 from counterpart application No. 11172126.2 2305, 6 pages total.
Silke Ulrich et al., "Development of an optimization concept for arc-modulated cone beam therapy", Physics in Medicine and Biology, 52 (2007), IOP Publishing, doi:10.1088/0031-9155/52/14/2006, (pp. 4099-4119, 21 pages total).
Yu, Cedric X., "Intensity Modulated Arc Therapy: Technology and Clinical Implementation", AbstractID: 10351 Title: Advances in Arc Therapy, 2000, 14 pages.

*Primary Examiner* — Jurie Yun (57) ABSTRACT

Some aspects include a system, apparatus, means and method for configuring a radiotherapy beam shaping device to define a treatment field of view, acquiring images of a patient area within the treatment field of view based on an imaging radiation beam, determining a treatment motion model that predicts, based on the acquired images, a prediction treatment period during which the patient area will be within the treatment field of view of the radiotherapy beam shaping device, and delivering a treatment radiation beam to the patient area for a time period equal to the prediction treatment period.

17 Claims, 7 Drawing Sheets

RADIATION TREATMENT OF MOVING TARGETS

BACKGROUND

1. Field

The embodiments described below relate generally to delivery of radiotherapy treatment. More specifically, some embodiments are directed to radiotherapy treatment of moving patient areas and systems for delivering such treatments.

2. Description

Radiotherapy or radiation therapy is used to treat cancer and other diseases with ionizing radiation. Conventional radiotherapy systems generate and direct a beam of radiation to a targeted treatment area within a patient volume. The radiation beam is intended to injure or destroy cells within the targeted area by causing ionizations within the cells or other radiation-induced cell damage.

Radiotherapy treatment plans are intended to maximize radiation delivered to a targeted area while minimizing radiation delivered to healthy tissue. In this regard, the treatment of a moving target area poses a challenge to radiotherapy. In some embodiments and contexts of radiotherapy, moving targets intended for treatment by radiation are commonly encountered. For example, stereotactic body radiation therapy (SBRT), which is becoming increasingly popular in the treatment of lung cancer, routinely encounters moving tumors due the motion induced by respiratory breathing.

Effective treatment of moving targets includes detecting and monitoring the motion of the target area, and delivering radiotherapy beams to the moving target. A number of conventional technologies may be used to detect and monitor target motion. Some techniques include providing a device to monitor the rise and fall of an external surface of the patient caused by breathing, while other techniques include providing implantable beacon devices in a patient to directly monitor tumor motion without a surrogate. Some other technologies include using X-Ray imaging. However, each of these technologies for monitoring target motion is separate and distinct from the radiotherapy treatment system and requires devices and/or systems internal or external to the patient.

One conventional method for addressing the delivery of radiation treatment to moving targets includes using an increased margin of delivery around a target that is large enough to account for target excursions from a nominal position. While the increased margin may result in the target receiving a desired radiation dose, surrounding healthy tissue or organs are at an increased risk of also receiving radiation. Gated treatment techniques to address moving targets involve determining a gating window during which the target movement is minimized to deliver the radiation treatment. For example, radiation may be delivered to the target only when the patient is within 80% exhalation of the breathing cycle, a period when motion of the targeted treatment area may be relatively motionless. However, acquisition of planning images (e.g., 4D CT computed tomography) and a breathing monitoring device to provide an indication of the phases of the patient's breathing cycle are needed for this technique. One proposed technique for delivering radiation to a moving target involves using an auxiliary device to determine the location and the shape of the target at any point in time and reshaping the MLC (multileaf collimator) leaves of the radiotherapy system to follow (i.e., track) the target shape at any point in time. However, this technique also requires an auxiliary device in addition to the radiotherapy system.

The present inventors have realized that conventional moving target monitoring and treatment delivery as described above is inefficient and insufficient for radiotherapy treatment of moving targets. In particular, since conventional techniques require additional, auxiliary, external, and/or internal devices and processes to detect, monitor and deliver radiation to a moving target, other systems to provide treatment of moving target areas are desired.

SUMMARY

In order to address the foregoing, some embodiments provide a system, method, apparatus, and means to configure a radiotherapy beam shaping device to define a treatment field of view, acquire images of a patient area within the treatment field of view based on an imaging radiation beam, determine a treatment motion model that predicts, based on the acquired images, a prediction treatment period during which the patient area will be within the treatment field of view of the radiotherapy beam shaping device, and deliver a treatment radiation beam to the patient area for a time period equal to the prediction treatment period.

According to some embodiments, the treatment radiation beam is delivered to the patient area for a time period equal to the prediction treatment period when the patient area is within the treatment field of view.

According to some aspects, the treatment field of view corresponds to a treatment volume for delivery of the radiation treatment beam. Furthermore, the radiotherapy beam shaping device may be configured to extend beyond the treatment field of view corresponding to the treatment volume for delivery of the radiation treatment beam. In some aspects, images of a patient area may be acquired based on an imaging radiation beam when the radiotherapy beam shaping device is configured to extend beyond the treatment field of view corresponding to a treatment volume for delivery of the radiation treatment beam, and the treatment radiation beam may be delivered to the patient area for a time period equal to the prediction treatment period when the radiotherapy beam shaping device is configured to the treatment field of view corresponding to a treatment volume for delivery of the radiation treatment beam.

Aspects may include acquiring of images of a patient area by delivering a burst of the imaging radiation beam to an imaging device and obtaining an output of the imaging device upon completion of the burst of the imaging radiation beam.

The appended claims are not limited to the disclosed embodiments, however, as those in the art can readily adapt the descriptions herein to create other embodiments and applications.

BRIEF DESCRIPTION OF THE DRAWINGS

Embodiments will become readily apparent from consideration of the following specification as illustrated in the accompanying drawings, in which like reference numerals designate like parts, and wherein.

DETAILED DESCRIPTION

The following description is provided to enable a person in the art to make and use some embodiments and sets forth the best mode contemplated by the inventors for carrying out some embodiments. Various modifications, however, will remain readily apparent to those in the art.

Figure 1:
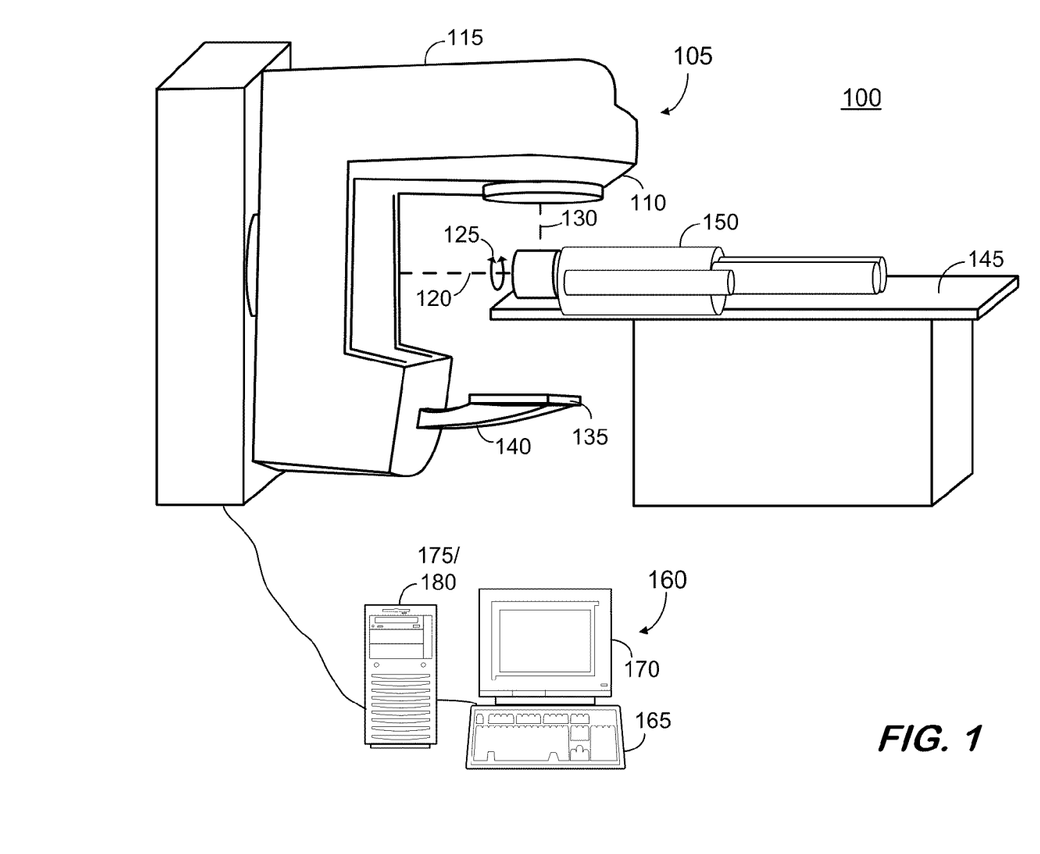
FIG. 1 is a perspective view of a treatment room according to some embodiments.

FIG. 1 illustrates radiotherapy treatment room 100 pursuant to some embodiments. Radiotherapy treatment room 100 includes linear accelerator (linac) 105, table 145 and operator console 160. The various components of radiotherapy treatment room 100 may be used to deliver a beam of radiation to a beam object such as patient 150. The patient may be positioned to receive the beam according to a radiation treatment plan. The elements of treatment room 100 may be employed in other applications according to some embodiments.

Linac 105 generates and emits a radiation beam (e.g., an x-ray beam) from treatment head 110. The radiation beam may comprise electron, photon or any other type of radiation. According to some embodiments, the beam exhibits energies in the megavoltage range (i.e. >1 MeV) and may therefore be referred to as megavoltage beam.

Treatment head 110 is coupled to a projection of gantry 115. Gantry 115 is controllable to be rotatable around gantry axis 120. As indicated by arrow 125, gantry 115 may rotate clockwise or counter-clockwise according to some embodiments. Rotation of gantry 115 serves to rotate treatment head 110 around axis 120.

During radiation emissions (e.g., treatment, imaging, calibration, and other procedures) treatment head 110 emits a divergent beam of megavoltage x-rays along beam axis 130. The beam is emitted towards the isocenter of linac 105. The isocenter may be located at the intersection of beam axis 130 and gantry axis 120. Due to divergence of the beam and the shaping of the beam by beam-shaping devices in treatment head 110, the beam may deliver radiation to a volume of patient 150 rather than only through the isocenter.

Table 145 may support a patient during radiation treatment and other aspects discussed herein. Table 145 may be adjustable to assist in positioning patient 150 or a particular target area and volume of the patient at the isocenter. Table 145 may also be used to support devices used for such positioning, for calibration and/or for verification.

Imaging device 135 may comprise any system to acquire an image based on radiation received at the imaging device. Imaging device 135 may be attached to gantry 115 in any manner, including an extendible and retractable housing 140. Rotation of gantry 115 may cause treatment head 110 and imaging device 135 to rotate around the isocenter such that the isocenter remains located between treatment head 110 and imaging device 135 throughout stationary and rotational movements of gantry 115.

Imaging device 135 may acquire projection images before, during and/or after radiation treatment. In some embodiments, imaging device 135 may include an analog or a digital radiation detector. Imaging device 135 may be used to acquire images based on radiation emitted from treatment head 110. These images may reflect the attenuative properties of objects located between treatment head 110 and imaging device 135. Such projection images may be used to determine imaging geometry parameters associated with the imaging system comprising treatment head 110 and imaging device 135. The two-dimensional projection images and/or three-dimensional images reconstructed based on the projection images may be used to detect, monitor, and record a target area or volume (e.g., a tumor) position and a movement of the target area or volume.

Operator console 160 includes input device 165 for receiving instructions from an operator such as an instruction to calibrate linear accelerator 105 and an instruction to configure the beam shaping device of treatment head 110 (e.g., a collimator) with a particular field of view for a particular interval of time. Console 160 also includes output device 170 that may include a monitor for presenting acquired three-dimensional images, operational parameters of linear accelerator 105 and/or interfaces for controlling elements thereof. Input device 165 and output device 170 are coupled to processor 175 and storage 180.

Processor 175 executes program code according to some embodiments. The program code may be executable to control linear accelerator 105 to operate as described in various methods and processes herein. The program code may be stored in storage 180, which may comprise one or more storage media of identical or different types, including but not limited to a fixed disk, a floppy disk, a CD-ROM, a DVD-ROM, an optical disk disk, a magnetic tape, a solid state storage device, a flash drive, and a signal. Storage 180 may store, for example, initial imaging geometry parameters, radiation treatment plans, projection images, software applications to calibrate linear accelerator 105 and/or to provide radiation treatment, and other data used to perform radiation treatment.

Operator console 160 may be located apart from linear accelerator 105, such as in a different room, in order to protect its operator from radiation. For example, linear accelerator 105 may be located in a heavily shielded room, such as a concrete vault, which shields the operator from radiation generated by accelerator 105.

Each of the devices shown in FIG. 1 may include fewer or more elements than those shown and are not limited to the devices shown in FIG. 1.

Figure 2:
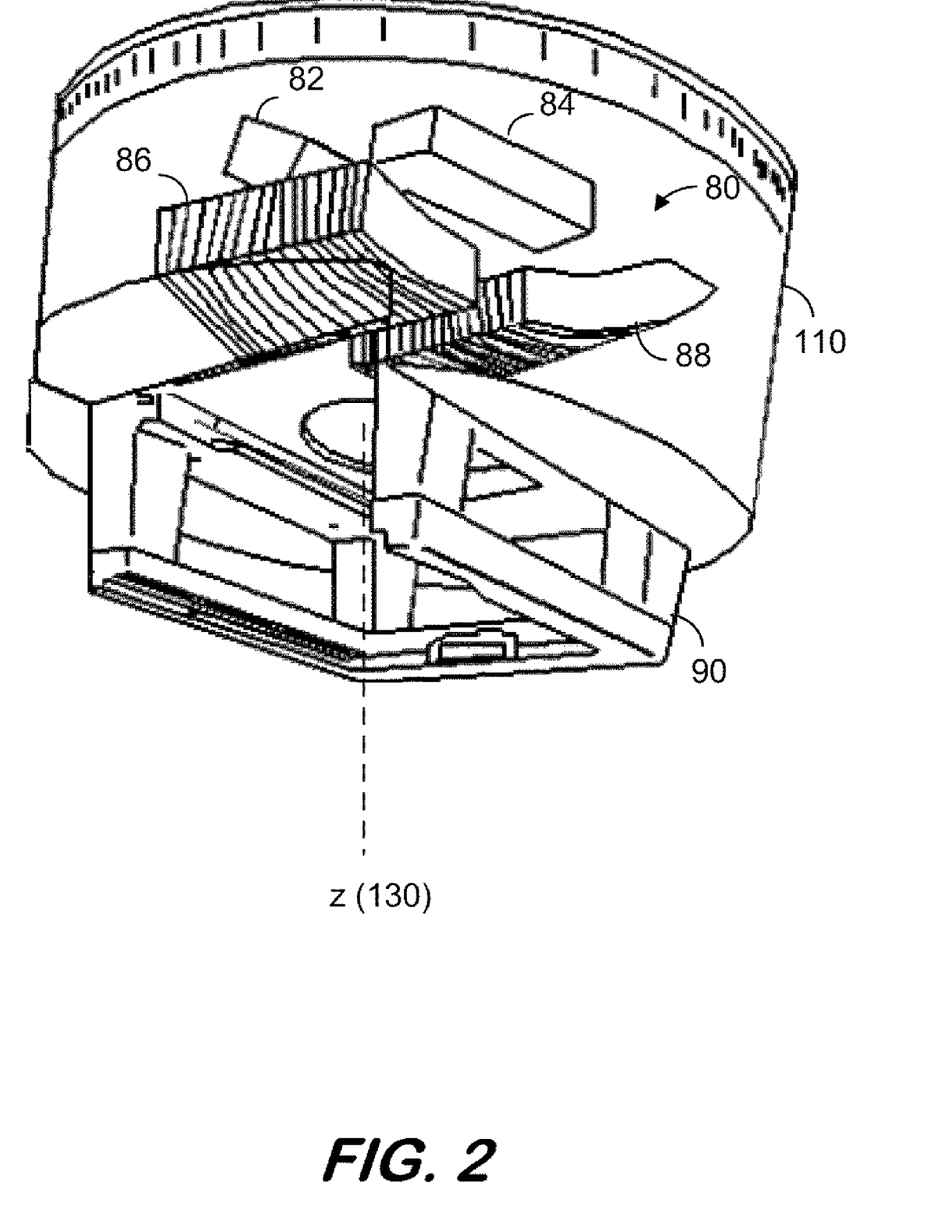
FIG. 2 is a depiction of a beam shaping device in accordance with some embodiments.

FIG. 2 illustrates treatment head 110 according to some embodiments. Treatment head 110 includes a beam shaping device, collimator 80, that may be used to shape a radiation beam to conform to an aperture specified by a treatment plan. Collimator 80 includes a pair of jaws (Y-jaws) 82 and 84 and a pair of jaws (X-jaws) 86 and 88. The positioning of X-jaws 86 and 88 and Y-jaws 82 and 84 determines a size and shape of an opening (i.e, a field of view) through which a radiation beam may pass along axis 130.

Each pair of jaws 86/88 and 82/84 is rotatable about axis 130. As depicted in FIG. 2, X-jaws 86 and 88 may be formed of a plurality of individual elements. These individual elements may be movable along a path intersecting axis 130. Movement of each element may be individually controllable to generate a wide variety of aperture shapes.

Treatment head 110 also includes accessory tray 90. Accessory tray 90 may be configured to receive and securely hold attachments used during the course of treatment planning and treatment (such as, for example, reticles, wedges, or the like). According to some embodiments, treatment head 110 is rotatable to rotate collimator 80 and accessory tray 90 around axis 130 while maintaining the physical relationships between X-jaws 86 and 88, Y-jaws 82 and 84, and accessory tray 90.

Figure 3:
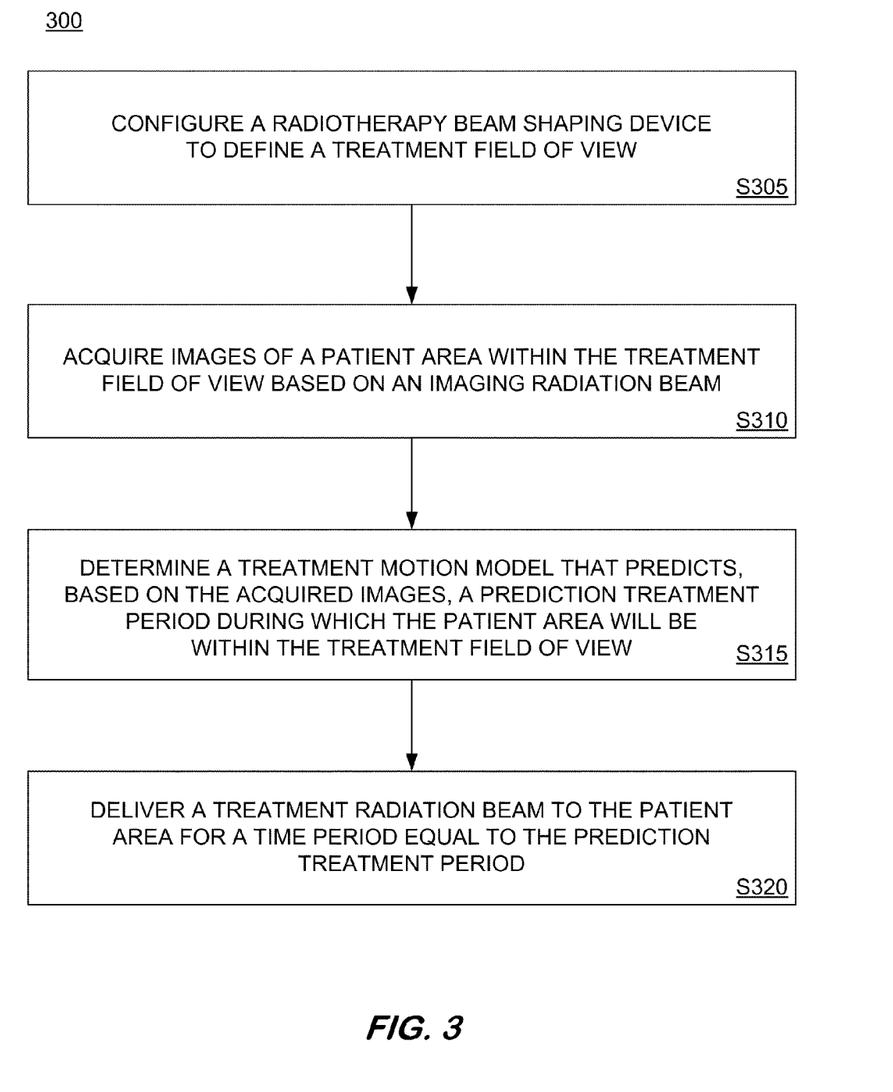
FIG. 3 is a flow diagram of a process according to some embodiments.

FIG. 3 is a flow diagram of a process 300 according to some embodiments. Process 300 and the other processes described herein may be performed using any suitable combination of hardware, software or manual means. Software embodying these processes may be stored by any medium, including a fixed disk, a floppy disk, a CD-ROM, a DVD-ROM, a Zip™ disk, a magnetic tape, a solid state storage device, or a signal. Examples of these processes will be described below with respect to the elements of radiotherapy treatment room 100, but embodiments are not limited thereto.

In some embodiments, and prior to S305, an operator may interact with input device 165 of operator console 160 to initiate operation of linear accelerator 105 to execute a radiotherapy treatment plan. In response to the user interaction, processor 175 may execute program code or instructions of a system control application stored in storage 180. The operator may further operate input device 165 to initiate radiation of a patient area (e.g., a tumor) of patient 150, including moving patient areas. Some aspects of the initiation may include positioning patient 150, gantry 115, and imaging device 135 at a position and angle for treatment, according to a treatment plan.

At S305, with the patient, gantry, and imaging device at a position and angle for treatment, the radiotherapy beam shaping device of linear accelerator 105 is configured to define a field of view. The field of view defined by the radiotherapy beam shaping device limits the area of the patient that will be exposed to radiation during an emission of an imaging or treatment radiation beam. In some aspects, the field of view is shaped according to a treatment plan and corresponds to a treatment volume of the patient that is to receive treatment radiation. In some embodiments, the field of view may be larger than a silhouette of the patient area by a predetermined margin of error. In the instance the field of view corresponds to a treatment volume, including a predefined margin of error, the field of view may also be referred to as a treatment field of view herein.

At S310, images of a targeted patient area within the field of view are acquired. Acquisition of the images may include adjusting or otherwise tuning the radiation beam emitted by treatment head 110 of linear accelerator 105 to an energy and dose rate appropriate for imaging. In some embodiments, a megavoltage (MV) beam is used for imaging. In some aspects, MV cine images of the patient area are obtained for monitoring the movement of the patient area within the field of view, but embodiments are not limited thereto.

At S315, process 300 determines a treatment motion model based on the acquired images. The treatment motion model may be based on a mathematical modeling technique that predicts the treatment period or interval of time during which the patient area will be within the field of view of the radiotherapy beam shaping device.

At S320, a treatment radiation beam is delivered to the patient area for a time period equal to the prediction time period. In this manner, the treatment radiation will be delivered to the patient area for the time interval the treatment area is within the field of view. Accuracy of the prediction time period may be assured by continually monitoring the motion of the patient area in the field of view and, if need be, dynamically adjusting the prediction time period. Operation S320 may include adjusting the treatment radiation beam to an energy and dose rate as prescribed by a treatment plan. In some aspects, the energy and dose rate of the treatment radiation beam may be adjusted based, at least in part, on the prediction time period determined based on the acquired images of the moving patient area.

In some embodiments, process 300, including operations S310, S315, and S320, may be repeated until the prescribed dose for the patient area is delivered thereto. Upon delivery of the prescribed dose to the patient area, gantry 115 may be advanced to a next treatment angle according to the treatment plan, wherein process 300 may be repeated to further monitor and deliver radiotherapy treatment to the patient area.

Figure 4:
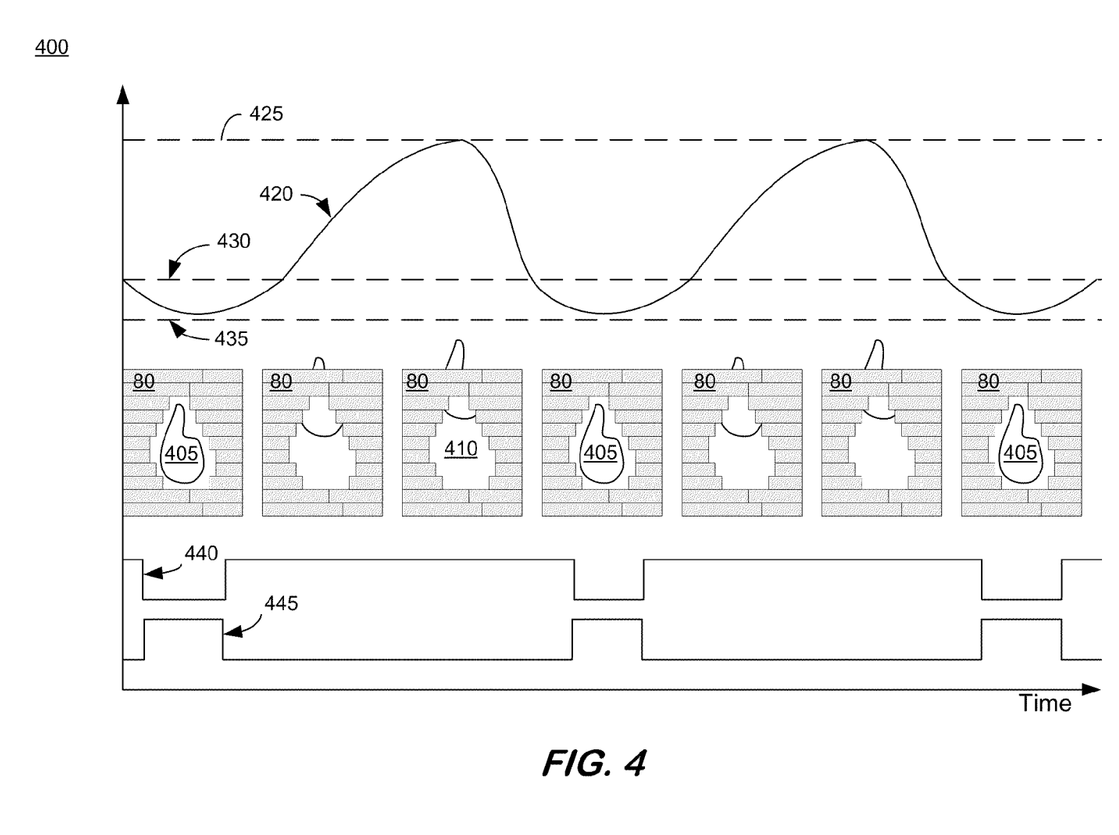
FIG. 4 is a timing diagram according to some embodiments.

FIG. 4 provides a timing diagram for monitoring and delivering radiotherapy treatment to a moving patient area, according to some embodiments. In some embodiments, the timing diagram of FIG. 4 may relate to process 300. Timing diagram 400 illustrates the motion of a patient area, tumor 405, caused by breathing. The timing diagram includes a depiction of the motion of patient area 405 relative to the field of view 410 defined by a particular configuration of beam shaping device 80. As illustrated, there is a margin of error included in the field of view 410 around patient area 405, even when the patient area is well within the field of view. The field of view may correspond to a treatment volume according to a treatment plan. In the embodiment of FIG. 4, field of view 410 corresponds to a treatment volume according to a treatment plan and may be referred to herein as a treatment field of view.

Timing diagram 400 also includes a depiction of the breathing cycle of the patient as represented by respiratory signal 420. Respiratory signal 420 is derived from MV cine images acquired based on an imaging radiation beam. Accordingly, no auxiliary external or internal devices or systems are needed for detecting and monitoring the motion of patient area 405 in some embodiments herein.

As shown in FIG. 4, patient area 405 is well within treatment field of view 410 when the breathing cycle is between 80% exhalation (i.e., line 430) and 100% exhalation (i.e., line 435). During this period of time, it is seen that patient area 405 is relatively motionless and well within treatment field of view 410. For other portions of the breathing cycle up to 100% inhalation (i.e., line 425), patient area 405 moves at least partially out of treatment field of view 410. The period of time between 80% exhalation and 100% exhalation may correspond to the prediction treatment time, according to some embodiments.

Timing diagram 400 also includes line 440 that represents a timing of the delivery of the imaging radiation beam, according to some embodiments. Line 445 represents a timing of the delivery of the treatment radiation beam, according to some embodiments. As shown, the imaging radiation beam and the treatment radiation beam are delivered in an interlaced or alternating manner. As such, the imaging radiation beam and the treatment radiation beam may be generated and emitted by the same treatment head 110.

Figure 5:
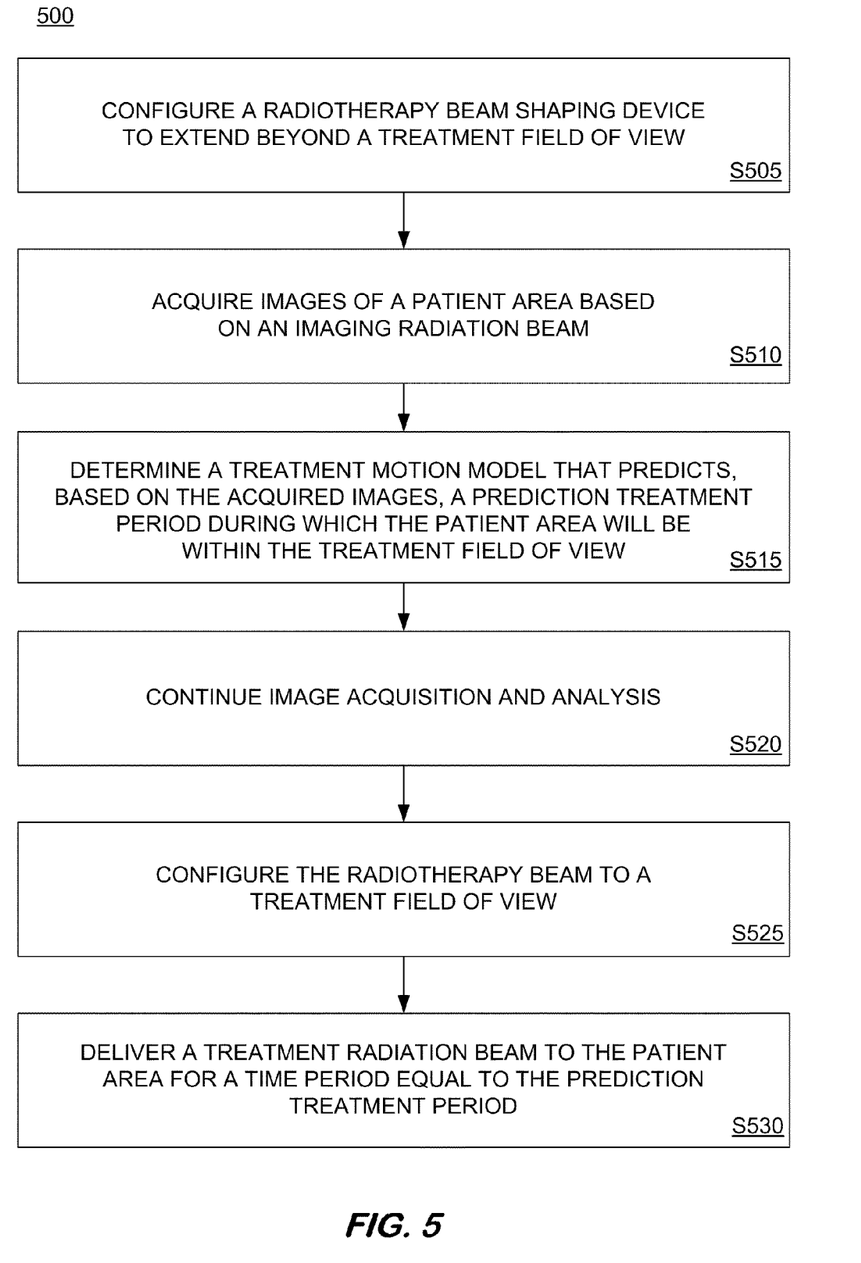
FIG. 5 is a flow diagram according to some embodiments.

FIG. 5 is a flow diagram of a process 500 according to some embodiments. In some embodiments, and prior to S505, an operator may interact with input device 165 of operator console 160 to initiate operation of linear accelerator 105 to execute a radiotherapy treatment plan. In response to the user interaction, processor 175 may execute program code or instructions of a system control application stored in storage 180. The operator may further operate input device 165 to initiate radiation of a patient area (e.g., a tumor) of patient 150, including moving patient areas. Some aspects of the initiation may include positioning patient 150, gantry 115, and imaging device 135 at a position and angle for treatment, according to a treatment plan.

FIG. 5 will be discussed in conjunction with FIG. 6 that provides a timing diagram for monitoring and delivering radiotherapy treatment to a moving patient area, according to some embodiments. In some embodiments, the timing diagram of FIG. 6 may relate to process 500, but is not limited to such embodiments.

At S505, with the patient, gantry, and imaging device at a position and angle for treatment, the radiotherapy beam shaping device of linear accelerator 105 is configured to extend beyond a treatment field of view. As mentioned hereinabove, the treatment field of view corresponds to a treatment volume of the patient that is to receive treatment radiation, including in some instances a margin of error.

Operation S505 is illustrated in timing diagram 600 where beam shaping device 615 is shown extended beyond treatment field of view 610 for various configurations of the beam shaping device. For example, in FIG. 6 beam shaping device 80 is shown extended beyond treatment field of view 610 at, for example, beam shaping configurations 650 and 655.

Process 500 continues at S510 where images of patient area 605 within the field of view 645 are acquired based on an imaging radiation beam delivered to imaging device 135. Acquisition of the images may include adjusting or otherwise tuning the radiation emitted by treatment head 110 of linear accelerator 105 to an energy and dose rate appropriate for imaging. In some embodiments, MV cine images of the patient area are obtained for monitoring the movement of the patient area within the field of view 645, but embodiments are not limited thereto.

Figure 6:
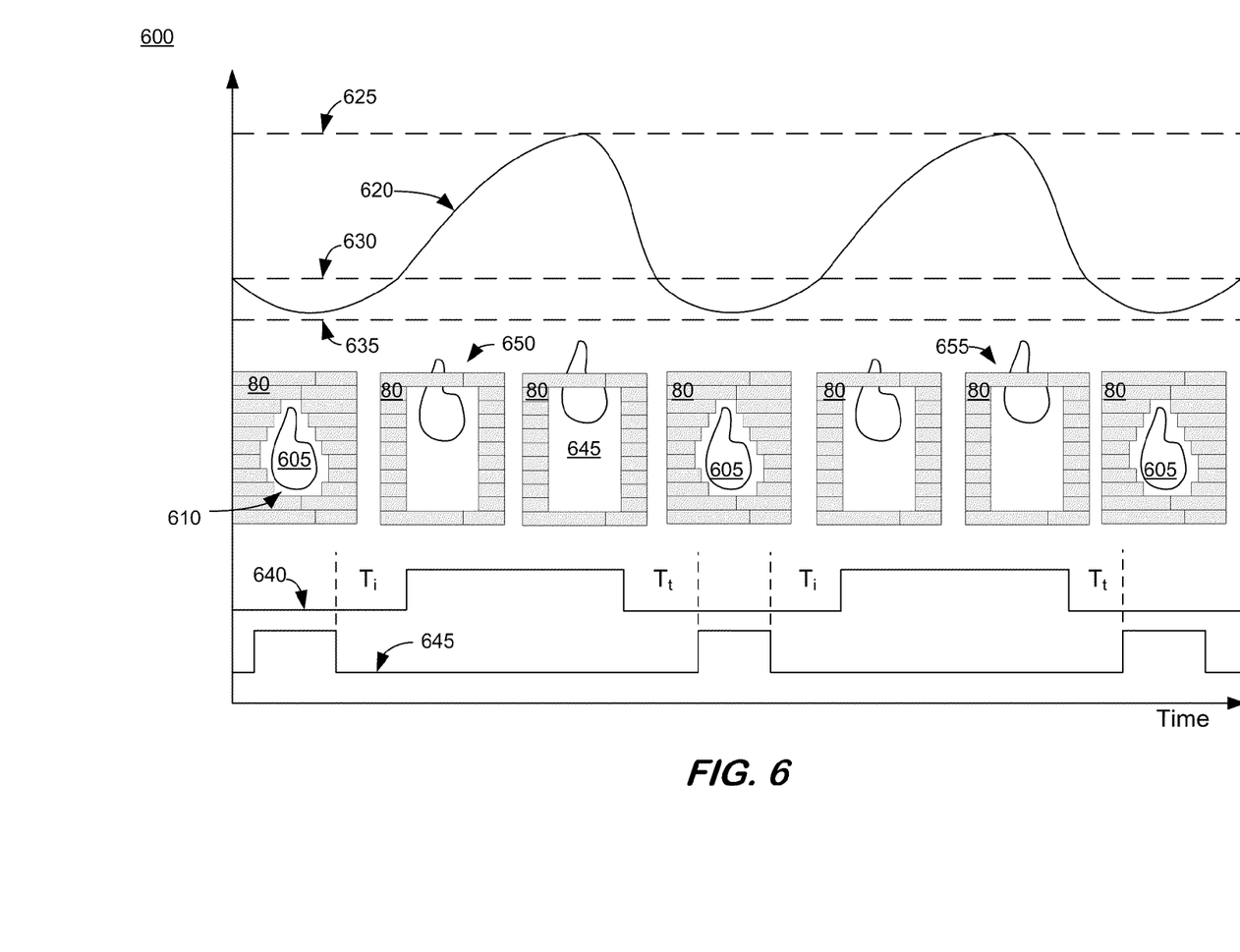
FIG. 6 is a timing diagram according to some embodiments.

As indicated by line 635 in FIG. 6, imaging radiation is delivered by treatment head 110 for imaging field of view 645 when beam shaping device 80 is extended beyond treatment field of view 610. It is further shown that the imaging radiation is not delivered during a time period $T_t$ equal to the time needed to configure beam shaping device 615 for imaging purposes.

At S515, process 500 determines a treatment motion model based on the acquired images. The treatment motion model may be based on a mathematical modeling technique that predicts the treatment period or interval of time during which the patient area will be within the field of view of the radiotherapy beam shaping device. In some embodiments, the treatment motion model predicts the treatment period during which patient area 605 will be within a field of view corresponding to treatment field of view 610.

At operation S520, image acquisition and analysis continues by further acquiring images based on an imaging radiation beam delivered to imaging device 135. The continued image acquisition may be useful in further monitoring the motion of patient area 605 and refining the treatment motion model.

At S525, beam shaping device 80 is configured to define a treatment field of view corresponding to a treatment volume according to the treatment plan. Referring to FIG. 6, beam shaping device 615 is configured to define a treatment field of view at 610. As illustrated, the period of time during which patient area 605 will be within a field of view 610 may occur with when breathing cycle 620 of the patient is between 80% exhalation (i.e., line 630) and 100% exhalation (i.e., line 635). During this period of time, it is seen that patient area 605 is relatively motionless and well within treatment field of view 610. For other portions of the breathing cycle up to 100% inhalation (i.e., line 625), patient area 605 moves at least partially out of the field of views 610 and 645. The period of time between 80% exhalation and 100% exhalation may correspond to the prediction treatment time, according to some embodiments.

With reference to FIG. 5, process 500 continues to S530 where a radiation beam is delivered to patient area 605 for a time period equal to the prediction time period. In some embodiments, the treatment radiation will be delivered to the patient area for the time interval the patient area is predicted to be within treatment field of view 610. Operation S530 may include adjusting the treatment radiation beam to an energy and dose rate as prescribed by a treatment plan. In some aspects, the energy and dose rate of the treatment radiation beam may be adjusted based, at least in part, on the prediction time period determined based on the acquired images of the moving treatment area.

FIG. 6 further illustrates treatment radiation is delivered to patient area 605 when the patient area is within treatment field of view 610 for a period of time predicted by the treatment motion model. As indicated by line 645, treatment radiation is delivered by treatment head 110 to patient area 605 when beam shaping device 80 is configured to treatment field of view 610. Timing diagram 600 also shows the imaging radiation is not delivered during a time period $T_t$ equal to the time needed to configure beam shaping device 615 for treatment purposes.

In some embodiments, process 500 may be repeated until the prescribed dose for the patient area is delivered. Upon delivery of the prescribed dose to the patient area 605, gantry 115 may be advanced to a next treatment angle according to the treatment plan wherein process 500 may be repeated to further monitor and deliver radiotherapy treatment to the patient area.

In some embodiments, the MV cine images discussed herein may be acquired by administering an imaging radiation beam of an appropriate tumor monitoring energy and dose rate to imaging device 135 operating in a continuous of free-running mode. However, imaging artifacts may result from the interference caused by the emission of the MV imaging radiation beam and the internal free-running frequency of imaging device 135 operating in the free-running mode.

In some embodiments, the MV cine images herein may be acquired by synchronizing an exposure of imaging device 135 with a readout thereof. More particularly, imaging device 135 may be exposed to a short burst of MV imaging radiation and, upon completion of the burst of MV imaging radiation, imaging device 135 may be triggered or invoked to provide an output of the imaging device. The process of exposing and reading an output of imaging device 135 may occur repeatedly at a fast rate. The rate of the synchronized exposures and readouts may depend, at least in part, on the exposure time needed to produce an image (i.e., dose needed per image) and a time needed for obtaining the output of imaging device 135. In this manner, imaging artifacts that may have been caused by an interference due to a simultaneous exposure of the imaging device and obtaining outputs of the imaging device may be avoided.

Figure 7:
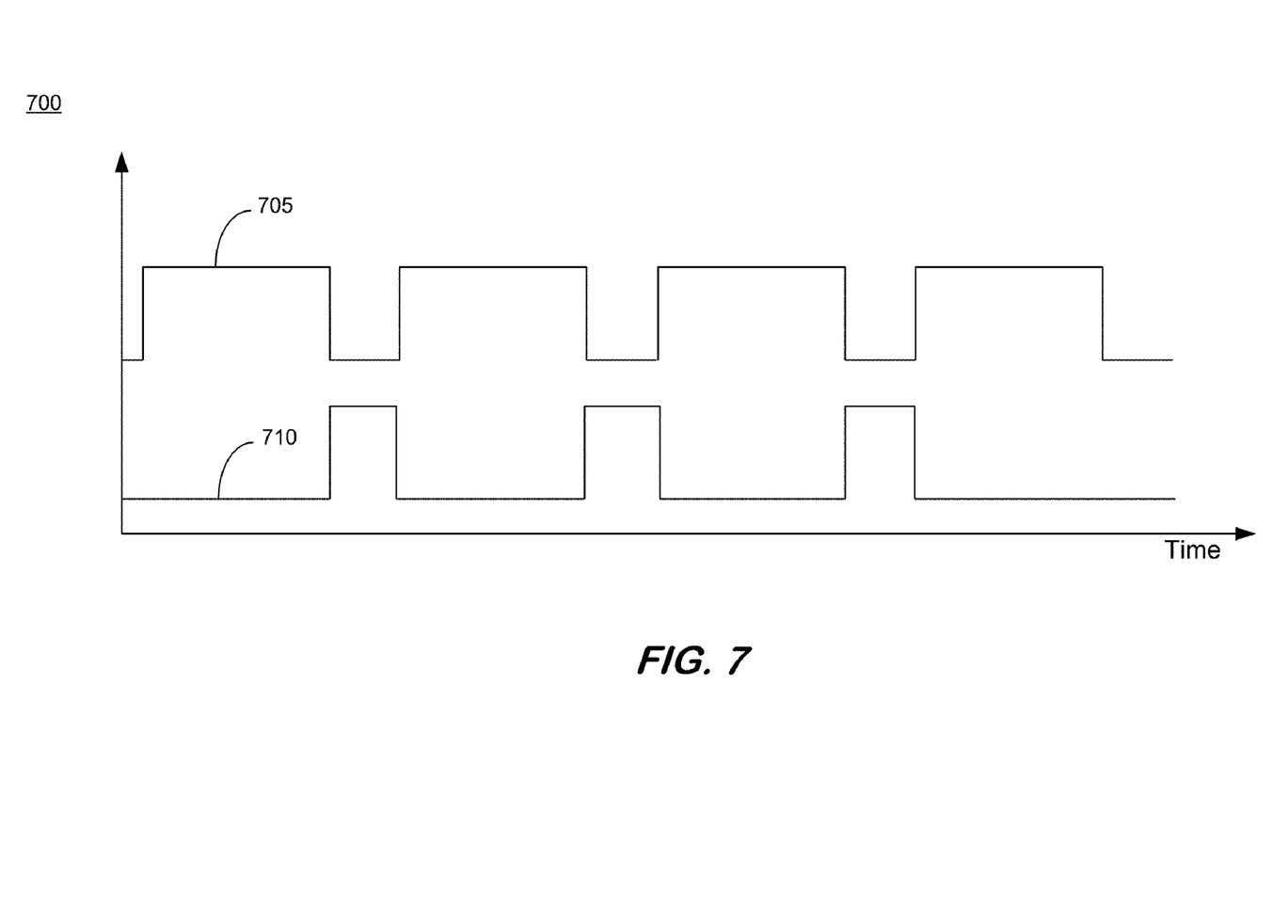
FIG. 7 is a timing diagram of an imaging process according to some embodiments.

FIG. 7 is a timing diagram related to a synchronized delivery of imaging radiation and a readout of the images from the imaging device 135. As shown, imaging radiation is emitted by treatment head 110 for short bursts of time (i.e., line 705), and at the completion of the burst of imaging radiation, imaging device 135 is triggered for a readout of the imaging device (i.e., line 705). In some embodiments, the synchronized sequencing of the imaging radiation emissions and the panel readouts may occur repeatedly (i.e., continuously) at a fast rate. In some embodiments, the panel readout takes about 67 msecs.

The several embodiments described herein are solely for the purpose of illustration. Therefore, persons in the art will recognize from this description that other embodiments may be practiced with various modifications and alterations.

What is claimed is:

1. A method comprising:
  configuring, for a gantry at a position and angle for treatment and having an emission device to emit an imaging radiation beam and a treatment radiation beam coupled thereto, a radiotherapy beam shaping device to define a treatment field of view;

acquiring images of a patient area within the treatment field of view based on the imaging radiation beam;

determining a treatment motion model that predicts, based on the acquired images, a prediction treatment period during which the patient area will be within the treatment field of view of the radiotherapy beam shaping device; and delivering the treatment radiation beam to the patient area for a time period equal to the prediction treatment period.

2. The method of claim 1, further comprising:
generating the imaging radiation beam for imaging the patient area within the treatment field of view.

3. The method of claim 1, wherein the treatment radiation beam is delivered to the patient area for a time period equal to the prediction treatment period when the patient area is within the treatment field of view.

4. The method of claim 1, further comprising:
determining the patient area is within the treatment field of view.

5. The method of claim 1, wherein the patient area moves, at least partially, within the treatment field of view.

6. The method of claim 1, wherein the treatment field of view corresponds to a treatment volume for delivery of the treatment radiation beam.

7. The method of claim 6, further comprising:
configuring the radiotherapy beam shaping device to extend beyond the treatment field of view corresponding to the treatment volume for delivery of the treatment radiation beam.

8. The method of claim 7, wherein:
the images of a patient area are acquired based on the imaging radiation beam when the radiotherapy beam shaping device is extended beyond the treatment field of view corresponding to the treatment volume for delivery of the treatment radiation beam; and the treatment radiation beam is delivered to the patient area for a time period equal to the prediction treatment period when the radiotherapy beam shaping device is configured to the treatment field of view corresponding to the treatment volume for delivery of the treatment radiation beam.

9. The method of claim 1, wherein the acquiring of images of a patient area comprises:
delivering a burst of the imaging radiation beam to an imaging device; and
obtaining an output of the imaging device upon completion of the burst of the imaging radiation beam.

10. A system comprising:
a gantry at a position and angle for treatment;
an emission device coupled to the gantry to emit an imaging radiation beam and a treatment radiation beam;
a radiotherapy beam shaping device to define a treatment field of view;
an imaging device coupled to the gantry to detect images of a patient area within the treatment field of view based on the imaging radiation beam; and
a processor to:
determine a treatment motion model that predicts, based on images detected by the imaging device using the imaging radiation beam, a prediction treatment period during which the patient area will be within the treatment field of view of the radiotherapy beam shaping device; and
cause the emission device to deliver the treatment radiation beam to the patient area for a time period equal to the prediction treatment period.

11. The system of claim 10, further comprising the processor to:
cause the emission device to emit the imaging radiation beam for imaging the patient area within the treatment field of view.

12. The system of claim 10, wherein the treatment radiation beam is delivered to the patient area for a time period equal to the prediction treatment period when the patient area is within the treatment field of view.

13. The system of claim 10, further comprising the processor to:
determine when the patient area is within the treatment field of view.

14. The system of claim 10, wherein the treatment field of view corresponds to a treatment volume for delivery of the treatment radiation beam.

15. The system of claim 14, wherein the radiotherapy beam shaping device is configured to extend beyond the treatment field of view corresponding to the treatment volume for delivery of the treatment radiation beam.

16. The system of claim 15, wherein:
the images of a patient area are detected by the imaging device based on the imaging radiation beam when the radiotherapy beam shaping device is configured to extend beyond the treatment field of view corresponding to the treatment volume for delivery of the treatment radiation beam; and the treatment radiation beam is delivered to the patient area for a time period equal to the prediction treatment period when the radiotherapy beam shaping device is configured to correspond to the treatment volume for delivery of the treatment radiation beam.

17. The system of claim 10, wherein:
the emission device emits a finite burst of the imaging radiation beam to the imaging device; and
the imaging device provides, upon completion of the emission of the finite burst of the imaging radiation beam, an output based on the finite burst of the imaging radiation beam.

* * * * *